United States Patent

Brunner

[11] Patent Number: 5,679,856
[45] Date of Patent: Oct. 21, 1997

[54] PROCESS FOR PREPARING DIPHENYLAMINES

[75] Inventor: Frédéric Brunner, Chézard, Switzerland

[73] Assignee: Ciba-Geigy Corporation, Tarrytown, N.Y.

[21] Appl. No.: 600,693

[22] Filed: Feb. 13, 1996

[30] Foreign Application Priority Data

Feb. 14, 1995 [CH] Switzerland ............... 432/95
May 18, 1995 [CH] Switzerland ............... 1475/95

[51] Int. Cl.$^6$ ............... C07C 211/55
[52] U.S. Cl. ............... 564/433
[58] Field of Search ............... 564/433

[56] References Cited

U.S. PATENT DOCUMENTS

| | | | |
|---|---|---|---|
| 4,517,388 | 5/1985 | Braverman | 568/779 |
| 4,804,783 | 2/1989 | Nagata et al. | 564/402 |
| 5,412,150 | 5/1995 | Wassel et al. | 560/56 |

FOREIGN PATENT DOCUMENTS

| | | |
|---|---|---|
| 0420556 | 4/1991 | European Pat. Off. . |
| 0429975 | 6/1991 | European Pat. Off. . |
| 1118213 | 10/1964 | Germany . |
| 4318069 | 3/1994 | Germany . |
| 1213249 | 11/1970 | United Kingdom . |

Primary Examiner—Ba K. Trinh
Attorney, Agent, or Firm—Kevin T. Mansfield

[57] ABSTRACT

A process is described for preparing diphenylamines of the formula

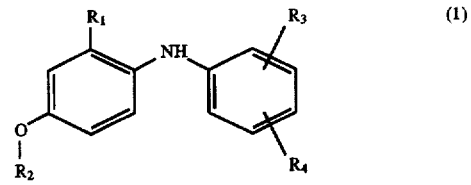

by oxybromination of a phenol ether compound using elemental bromine in the presence of hydrogen peroxide and of a catalyst to give a brominated phenol ether compound which is subsequently reacted with a formanilide compound to give the compound of the formula (1).

The oxybromination reaction is a regioselective, environmentally friendly and cost-efffective method of preparing brominated aromatic compounds.

The diphenylamines of the formula (1) are industrially useful intermediates for the production, for example of dyes, and in particular of color formers of the fluoran type for pressure- or heat-sensitive recording systems.

5 Claims, No Drawings

PROCESS FOR PREPARING DIPHENYLAMINES

The present invention relates to a process for preparing diphenylamines of the formula

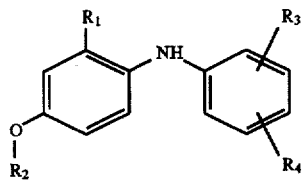
(1)

in which $R_1$ and $R_2$, independently of one another, are lower alkyl; and $R_3$ and $R_4$, independently of one another, are lower alkyl or halogen.

The process for preparing diphenylamines of the formula (1) by oxybromination of a phenol ether compound of the formula

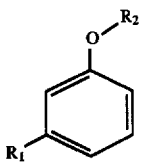
(2)

to the compound of the formula

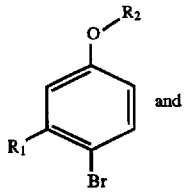
(3)

and reaction of the brominated phenol ether compound of the formula (3) under Ullmann coupling conditions with a compound of the formula

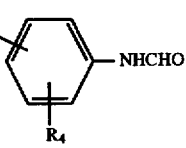
(4)

to give the compound of the formula (1) comprises carrying out the bromination of the phenol ether compound of the formula (2) to the compound of the formula (3) using elemental bromine and in the presence of hydrogen peroxide and if desired in the presence of a catalyst.

The overall reaction can be depicted by the following set of equations:

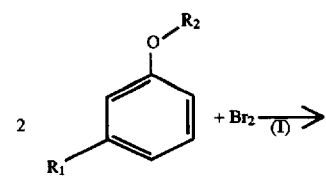

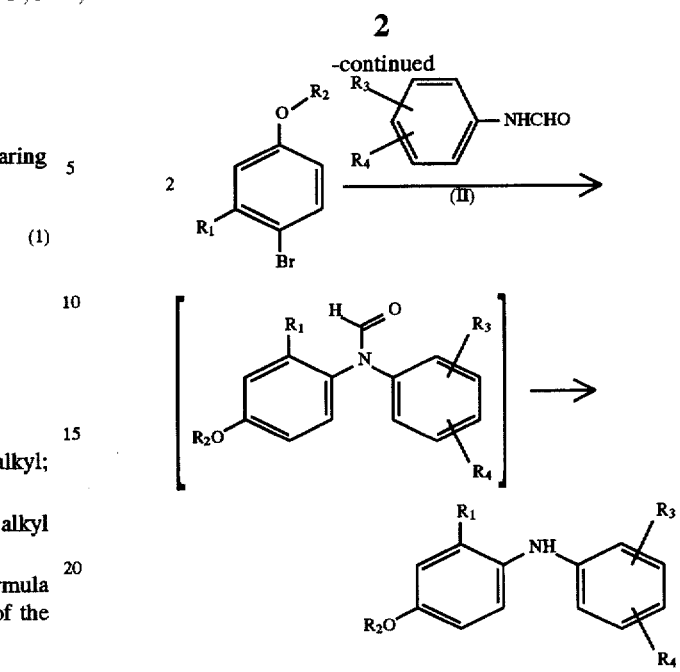

Lower alkyl radicals $R_1$, $R_2$ and $R_3$ are straight-chained or branched $C_1$–$C_5$alkanes, for example methyl, ethyl, propyl, isopropyl, butyl, tert-butyl or amyl. The radicals $R_1$, $R_2$ and $R_3$ are preferably ethyl and especially methyl.

Halogen is fluorine, bromine or, preferably, chlorine.

The preparation of the starting compound of the formula (2) is carried out in a manner known per se in accordance with the Williamson-synthesis by heating the corresponding sodium phenolate compound with an alkyl halide $R_2$-Hal in ethanolic or aqueous solution or, on the industrial scale, by treating the alkaline phenol solution with a dialkyl sulfate $(R_2)_2SO_2$. Examples of suitable starting compounds are m-cresol ethyl ether, m-cresol propyl ether or, preferably, m-cresol methyl ether.

The bromination of the phenol ether compound (reaction (I)) takes place preferably, for example, using two moles of the starting compound of the formula (2), elemental bromine, and two moles of hydrogen peroxide, with or without a catalyst such as, for example, an ammonium salt and, in particular ammonium molybdate. Other catalysts suitable for the process of the invention are those described, for example, in J.Chem.Soc.Chem.Comm. 19, 1421–1422 (1987).

In a particularly preferred embodiment the starting compound, the bromine and hydrogen peroxide are employed in stoichiometric ratios. In this case the reaction is usually carried out such that the phenol ether compound of the formula (2), the hydrogen peroxide, which is in the form for example of a 20 to 70% by weight solution, and, if used, the catalyst are initially introduced into acetic acid (98%) and the reaction mixture is stirred vigorously and cooled to about 0° C. The bromine, diluted with acetic acid, is subsequently added slowly dropwise. The reaction is highly exothermic and is carried out at a temperature of, for example, from −10° to 80° C., preferably from 0° to 5° C. The reaction time in this case is, for example, from 0.25 to 10 hours, preferably from 0.5 to 1 hour.

The resulting brominated phenol ether compound of the formula (3) is worked up in a manner known per se by separating off and concentrating the halogenated organic phase.

In the oxybromination process of the invention (reaction step (I) in the set of equations shown above), the bromination of the phenol ether compound of the formula (2) consumes only half an equivalent of bromine. Reaction (I) is therefore a regio selective, environmentally friendly and, furthermore, a cost-effective method of preparing brominated aromatic compounds.

In reaction (II), the brominated phenol ether compound of the formula (3) reacts with the formanilide of the formula (4) in the presence of copper and iodine and potassium carbonate, with evolution of $CO_2$, to give the diphenylamine of the formula (1). The temperature in this reaction step is, for example, from 120° to 250° C., and the reaction time is, for example, from 1 to 48 hours, preferably from 12 to 25 hours. In contrast to the Ullmann coupling, a mixture of diphenylformamide and diphenylamine is produced. The mixture of the two products is subsequently hydrolysed in aqueous potassium hydroxide solution to the desired diphenylamine of the formula (1). The diphenylamine is worked up in a manner known per se, for example by distillation, crystallization or extraction.

Reaction (II) is generally known and is described, for example, in Houben-Weyl, "Methoden der Organischen Chemie XII", page 32 to 42 (1957) or in "Organic Reactions III", page 19 to 24 (1965).

Using the present process it is possible, simply and with good yields, to obtain diphenylamines which are industrially useful intermediates for, for example, the preparation of dyes and, preferably, of colour formers of the fluoran type for pressure- or heat-sensitive recording systems. Starting from these diphenylamines and from hydroxybenzophenone-2'-carboxylic acids of the formula

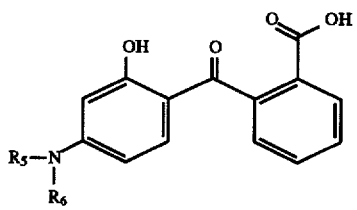

it is possible, for example, to prepare colour formers of the formula (7):

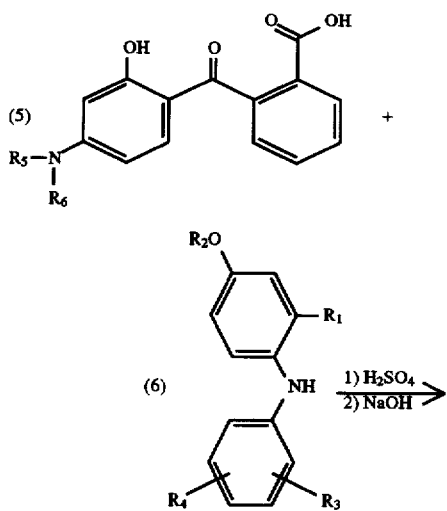

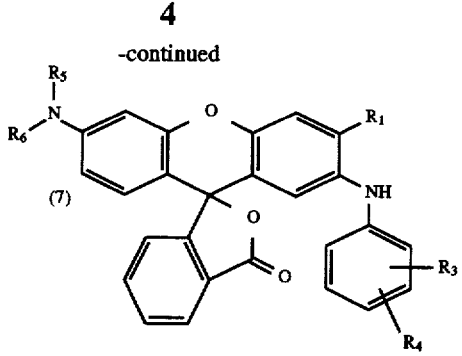

In the above equations, $R_5$ and $R_6$ independently of one another are lower alkyl, while $R_1$, $R_2$, $R_3$ and $R_4$ are as defined for the formulae (1), (2), (3) and (4).

Analogously, it is also possible to prepare colour formers of the formula

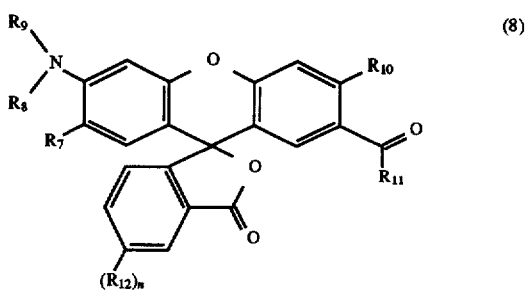

in which $R_7$ is hydrogen or $C_1-C_4$alkyl;

$R_8$ and $R_9$, independently of one another, are hydrogen; $C_1-C_8$alkyl; unsubstituted or $C_1-C_4$alkyl- or halogen-substituted $C_4-C_7$cycloalkyl; unsubstituted or $C_1-C_4$alkyl-, hydroxy-, or halogen-substituted phenyl; phenyl-$C_1-C_4$alkyl; $C_3-C_6$-alkenyl; $C_1-C_4$-alkoxy; $C_1-C_4$alkoxy-$C_1-C_4$alkyl; 2-tetrahydrofuranyl, or $R_8$ and $R_9$, together with the nitrogen atom to which they are attached, are an unsubstituted or $C_1-C_4$alkyl-substituted pyrrolidine, piperidine, morpholine, thiomorpholine or piperazine ring;

$R_{10}$ is hydrogen, hydroxyl or $C_1-C_4$alkyl;

$R_{11}$ is hydrogen; hydroxyl; $C_1-C_8$alkyl; $C_1-C_8$alkoxy; $C_1-C_8$haloalkyl; phenyl which is unsubstituted or substituted by halogen, $C_1-C_4$alkyl, $C_1-C_4$haloalkyl, $C_1-C_4$alkoxy; phenyl-$C_1-C_4$alkyl or phenyl-$C_1-C_4$alkoxy;

$R_{12}$ is halogen; nitro; $C_1-C_4$alkyl; $C_1-C_4$haloalkyl; amino; mono-$C_1-C_4$alkylamino; di-$C_1-C_4$alkylamino; or $COR_{11}$; and n is 0; 1; 2; 3; or 4.

Colour formers of the formula (7) and pressure- or heat-sensitive recording systems are known, for example, from U.S. Pat. No. 5,166,350, while colour formers of the formula (8) and pressure- or heat-sensitive recording systems are known from U.S. Pat. No. 5,395,948.

Colour formers of the formula (8) can also be prepared, if $R_{11}$ is $C_1-C_8$alkyl, by esterifying the compound of the formula

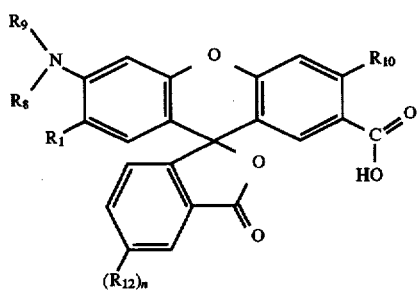

(8a)

In this case, esterifying agents which can be used are compounds having a $C_1$–$C_8$alkyl group, preferably an ethyl group, examples being $C_1$–$C_8$alkyl halides, preferably $C_1$–$C_8$-alkyl bromide, N,N-dimethylformamide di-$C_1$–$C_8$alkyl acetal, tetraalkyloxonium tetrafluoroborate or orthoformic acid tri-$C_1$–$C_8$alkyl esters. This variant preparation of the colour formers of the formula (8) is a further subject of the invention.

The examples which follow are intended to illustrate the invention without limiting it to them.

EXAMPLE 1

Preparation of 2-bromo-5-methoxytoluene 36.65 g (0.3 mol) of m-cresol methyl ether and 39.8 g (0.35 mol) of 30% hydrogen peroxide in 40 ml of acetic acid (98%) are initially introduced into a flask which has a volume of 250 ml and ground-glass joints and is fitted with an internal thermometer, stirrer and dropping funnel. The mixture is stirred vigorously and cooled to 0° C. Subsequently, bromine dissolved in 40 ml of 98% acetic acid is slowly added dropwise over 3 hours. The reaction is highly exothermic. During the period of dropwise addition, the reaction temperature is held constant at about 0° to 5° C. Following the end of dropwise addition, the temperature is raised to 20° C. and stirring is continued for one hour. The stirrer is then switched off and the mixture is left to stand at 20° C. Two phases immediately form. The lower organic, halogenated phase is separated off from the upper acetic acid phase and concentrated, to give 2-bromo-5-methoxytoluene of the formula

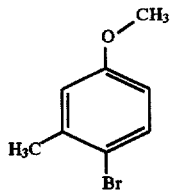

(101)

as a yellow oil.

Yield (crude): 58.12 g (96.3% of theory); GC analysis: 98.5% pure

EXAMPLE 2

Preparation of 4-methoxy-2-methyldiphenylamine 12.1 g (0.1 mol) of formanilide, 22.1 g (0.11 mol) of 2-bromo-5-methoxytoluene of the formula (101), 13.8 g (0.1 mol) of anhydrous potassium carbonate, 2.0 g (0.0079 mol) of iodine and 1.6 g (0.025 mol) of copper powder are initially placed in a 100 ml sulfonating flask fitted with an anchor stirrer, thermometer, condenser and oil bath, and the mixture is stirred. It is heated to 170° C. and then stirred at 170° C. for 22 hours, to give a black melt. This melt is then cooled to 80° C., a little toluene is added, and the solution is filtered. The residue is rinsed with toluene. The toluene filtrate is distilled with steam spray (distillate: water/toluene/unreacted 2-bromo-5-methoxytoluene) to leave a residue which comprises a mixture of black oil and water. The black oil is boiled under reflux for 25 hours with 250 g of 50% potassium hydroxide solution. The product obtained is extracted with toluene and washed with hot water. The toluene phase is dried over sodium sulfate, filtered and concentrated. The residue which remains comprises 17.0 g of the compound of the formula <img />

(102)

as black crystals.

Yield: 79.7% of theory.

EXAMPLES 3 TO 8

The procedure described in Examples 1 and 2 is followed, giving the compounds listed in Table 1.

TABLE 1

| Example/Compound of the formula | Phenol ether compound employed | Formanilide employed | Compound of the formula |
|---|---|---|---|
| 3 (103) | <img> (O—$C_2H_5$, $H_5C_2$) | <img> (—NHCHO) | <img> ($C_2H_5$, $C_2H_5O$, NH) |

TABLE 1-continued

| Example/Compound of the formula | Phenol ether compound employed | Formanilide employed | Compound of the formula |
|---|---|---|---|
| 4 (104) | 3-methyl anisole (O—CH₃ on benzene with H₃C at meta) | o-methyl formanilide (CH₃, NHCHO) | 2-methyl-N-(2-methylphenyl)-4-methoxyaniline derivative |
| 5 (105) | 3-methyl anisole | 2,4-dimethyl formanilide (H₃C—, CH₃, NHCHO) | corresponding diarylamine with two CH₃ and OCH₃ |
| 6 (106) | 3-ethyl phenetole (O—C₂H₅, H₅C₂) | o-methyl formanilide | diarylamine with C₂H₅, OC₂H₅, CH₃ |
| 7 (107) | 3-methyl anisole | p-methyl formanilide (H₃C—NHCHO) | diarylamine CH₃, CH₃O, CH₃ |
| 8 (108) | 3-ethyl phenetole | p-methyl formanilide | diarylamine C₂H₅, C₂H₅O, CH₃ |
| 8 (109) | 3-methyl anisole | 2,4-dichloro formanilide (Cl, Cl, NHCHO) | diarylamine CH₃, CH₃O, Cl, Cl |

EXAMPLE 9

Preparation of a fluoran colour former; esterification with ethyl bromide:

29.5 g of the water-moist product of the formula

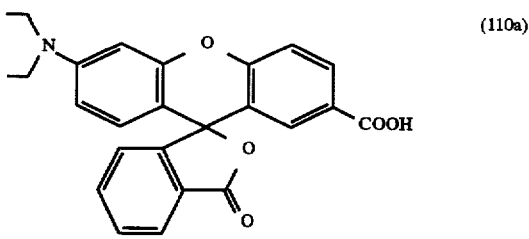

(110a)

(For preparation of this compound cf. U.S. Pat. No. 5,395, 948) are stirred in 46 ml of water and 0.5 g of tetrabutylammonium bromide at 25° C. 0.1 g of potassium iodide is added and the pH is adjusted to 10.4 with 15.5 ml of 10N sodium hydroxide solution. The mixture is simultaneously heated to 70°–75° C., during which a red solution is formed. 9.8 g of ethyl bromide are metered in uniformly at from 70° to 75° C. over the course of 8 hours and the pH is maintained at from 8 to 10 by adding a further 2.5 ml of 10N sodium hydroxide solution. The mixture is subsequently stirred at from 65° to 70° C. and constant pH for a further 15 hours and the precipitated product is filtered off and washed with a solution of sodium hydrogen carbonate, then with water and finally with methanol. Drying gives 19 g of the crystalline compound of the formula

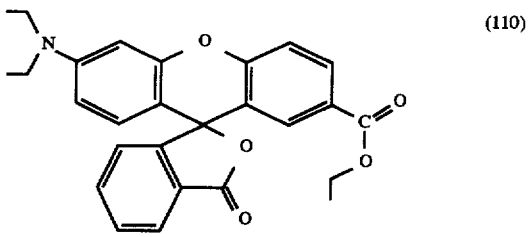

(110)

Melting point: 151°–153° C.

The product dissolves very well in the customary capsule oils and, as a colour former in both pressure and thermal processes, produces an intense orange colour.

EXAMPLE 10

Preparation of a fluoran colour former; esterification with N,N-dimethylformamide diethyl acetal;

2 g of the dry compound of the formula (110a) are dissolved at 80° C. in 30 ml of toluene. 1.3 g of N,N-dimethylformamide diethyl acetal are then added and the temperature is maintained at 90° C. for 90 minutes. The mixture is then concentrated on a rotary evaporator, the residue is taken up in 23 ml of hot isopropyl alcohol, the mixture is stirred until cold and the precipitate is obtained by filtration. Drying gives 1.5 g of the crystalline compound of the formula (110).

Melting point: 150°–151.5° C.

EXAMPLE 11

Preparation of a fluoran colour former; esterification with triethyl orthoformate 4 g of the dry compound of the formula (110a) are stirred into 26.7 g of triethyl orthoformate and the mixture is heated to 137° C. to form a solution. This solution is stirred at from 137° to 140° C. for 8 hours and then 20 g of the excess triethyl orthoformate are distilled off. The distillation residue (=5.6 g) is taken up in 56 ml of hot isopropyl alcohol, the mixture is stirred until cold and the precipitate is obtained by filtration. Drying gives 3 g of the crystalline compound of the formula (110).

Melting point: 147°–149° C.

EXAMPLE 12

Preparation of a fluoran colour former; esterification with triethyloxonium tetrafluoroborate 4 g of the dry compound of the formula (110a) are stirred at 25° C. into 75 ml of methylene chloride and 2 ml of N,N-diisopropylethylamine. 4 g of triethyloxonium tetrafluoroborate are introduced over one hour at 20°–25° C. and the mixture is subsequently stirred for 15 hours. The volatile constituents are then distilled off in vacuo, the residue is taken up in 50 ml of hot isopropyl alcohol, the mixture is clarified by filtration and the product is crystallized with cooling. Filtration and drying give 1.8 g of the compound of the formula (110).

Melting point: 149°–150° C.

What is claimed is:

1. A process for the preparation of a diphenylamine of the formula

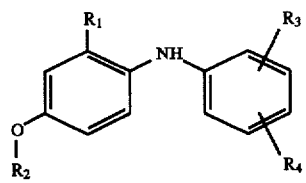

by oxybromination of a phenol ether compound of the formula

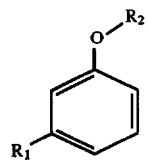

to the compound of the formula

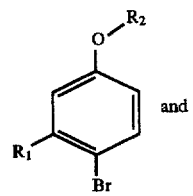

and reaction of the brominated phenol ether compound of the formula (3) under Ullmann coupling conditions with a compound of the formula

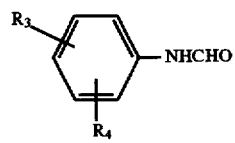

in which $R_1$ and $R_2$, independently of one another, are lower alkyl; and $R_3$ and $R_4$, independently of one another, are lower alkyl or halogen to give the compound of the formula (1), which comprises carrying out the bromination of the phenol ether compound of the formula (2) to the compound of the formula (3) using elemental bromine and in the presence of hydrogen peroxide and optionally in the presence of a catalyst.

2. A process according to claim 1, wherein the oxybromination is carried out at a temperature of from −10° to 80° C.

3. A process according to claim 1, wherein the reaction time for the oxybromination is from 0.25 to 10 hours.

4. A process according to claim 1, wherein during the oxybromination reaction hydrogen peroxide, the phenol ether of the formula (2) and the bromine are employed in stoichiometric quantities.

5. A process according to claim 1, wherein ammonium molybdate is employed as catalyst during the oxybromination.

* * * * *